United States Patent [19]

Chakrabarti et al.

[11] Patent Number: 4,694,104

[45] Date of Patent: Sep. 15, 1987

[54] PHASE TRANSFER CATALYSTS

[75] Inventors: Paritosh M. Chakrabarti, Cedar Grove; Sureshchandra G. Desai, Wayne; Lindley S. Wood, Jr., Montclair, all of N.J.

[73] Assignee: GAF Corporation, Wayne, N.J.

[21] Appl. No.: 406,755

[22] Filed: Aug. 9, 1982

[51] Int. Cl.$^4$ .............................................. C07C 91/26
[52] U.S. Cl. ..................... 564/285; 504/290; 570/186; 570/187; 570/182; 568/11; 560/226
[58] Field of Search ......................... 564/294, 285, 290; 568/11; 585/400; 570/186, 187, 182; 560/226

[56] References Cited

U.S. PATENT DOCUMENTS

| | | | |
|---|---|---|---|
| 2,944,902 | 7/1960 | Carroll et al. | 564/294 |
| 3,919,319 | 11/1975 | Hintermeier et al. | 564/294 |
| 4,134,970 | 1/1979 | Panke et al. | 564/294 |
| 4,281,196 | 7/1981 | Rutyen et al. | 564/294 |

FOREIGN PATENT DOCUMENTS 1084134  9/1967  United Kingdom ................ 564/294

OTHER PUBLICATIONS

Starks et al., "Phase Transfer Catalysis", pp. 224–287, Academic Press, (1978).

Primary Examiner—James H. Reamer

Attorney, Agent, or Firm—Marilyn J. Maue; Joshua J. Ward

[57] ABSTRACT

The invention relates to polyoxyalkylene quaternized salts as phase transfer catalysts for liquid/liquid phase cyclopropanation, substitution or addition reactions involving a normally liquid or solvent soluble olefinically unsaturated hydrocarbon and the process in which said quaternary compound is utilized. The involved quaternized salts are defined by the formula:

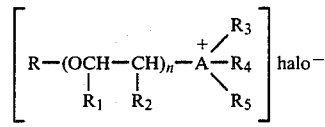

wherein
R is alkyl having 8 to 30 carbon atoms, blends thereof or alkyl-substituted phenyl of 10 to 24 carbon atoms;
n has a value of from 2 to 14 and includes mixtures within said range;
$R_1$ and $R_2$ are hydrogen atoms or one of $R_1$ and $R_2$ is methyl;
$R_3$, $R_4$ and $R_5$ are independently hydrogen, an alkyl radical of 1 to 6 carbon atoms or phenyl or one of $R_3$, $R_4$ and $R_5$ is an $\beta$-ethyl-alkali metal sulfonate;
A is a phosphorous or a nitrogen atom; and halo is a chlorine or bromine ion.

11 Claims, No Drawings

PHASE TRANSFER CATALYSTS

BACKGROUND OF THE INVENTION

It is known that in the chemistry of liquid/liquid phase reactions, the fundamental requirement for a bimolecular reaction to occur is collision, and that no amount of kinetic energy contained by one species can make it react with another if the reactants do not come into proximity. In the past, the problem of phase separation has traditionally been overcome by utilizing certain solvents, such as a dipolar aprotic solvent which provides mutual dissolution of both inorganic salts and organic substrates; however, the principle difficulty with this approach has been that the solvents are often costly, difficult to recover after completion of the reaction and hard to purify, dry and maintain in the required anhydrous state. An alternative to such a procedure involving specialized solvents, is the use of phase transfer catalysts such as quaternary phosphonium and ammonium halides to provide the desired two phase solubility and anion exchange with the inorganic species in the aqueous phase. Specifically in this catalysis, the aqueous phase, which contains the inorganic salt reservoir as a base or nucleophile, is contacted with the organic phase containing the organic substrate to be reacted with the salt through anion exchange of the inorganic salt with the quaternary catalyst and formation of a quaternary nucleophile soluble in the organic phase. The quaternized salt catalysts of the prior art have been highly effective in solvation by ion pair extraction of the $OH^-$ anion of the inorganic salt leading to formation of a dihalo carbene radical suitable for reaction with the organic coreactant. Obviously, in these reactions, the degree and/or rate at which the anion can be transferred into the organic phase is a most important factor. It has now been found that certain novel quarternary ammonium and phosphonium catalysts provide a more complete and/or rapid transfer of hydroxide or other anions to the reaction zone affording higher yields and shorter reaction times thereby enhancing the economy of the chemical process.

Accordingly, it is an object of this invention to provide a more efficient and effective phase transfer reaction with an improved catalyst.

A second object of the invention is to provide a more economical and commercially feasible process for effecting phase transfer reactions involving olefinically unsaturated compounds through the formation of a dihalo carbene.

These and other objects of the invention will become apparent from the following description and disclosure.

According to this invention, phase transfer reactions including cyclopropanation, substitution nucleophilic bimolecular displacement ($S_n 2$) and addition reactions are catalyzed with a polyoxyalkylene quaternized salt having the formula:

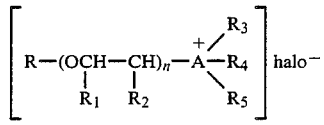

wherein

R is alkyl of 8 to 30 carbon atoms, blends thereof or alkyl-substituted phenyl of 10 to 24 carbon atoms;

n has a value of from 2 to 14 and includes mixtures within that range;

$R_1$ and $R_2$ are hydrogen atoms or one of $R_1$ and $R_2$ is methyl;

$R_3$, $R_4$ and $R_5$ are independently hydrogen, an alkyl radical of 1 to 6 carbon atoms or phenyl or one of $R_3$, $R_4$ and $R_5$ is an alkylene-alkali metal sulfonate;

A is a phosphorous or a nitrogen atom; and halo is a chlorine or bromine ion.

The improvements obtained with the present quaternized salt is mainly due to the polyether moiety which reduces the interfacial tension, thus affording a kinetic enhancement of ion-pair phase transfer. Because of the greater water affinity of the polyether moiety, as compared to the corresponding hydrocarbon, the present anion exchanged quaternary compound remains in or near the water/organic interface to provide a more rapid and complete transfer of the inorganic nucleophile and subsequent formation of the dihalo carbene required for contact with the organic coreactant in cyclopropanation reactions.

Because the polyether moiety of the present quaternary catalyst has an affinity for the water phase, the catalyst molecule affords surfactant properties, i.e. reducing interfacial tension, increasing the rate of replicate exchange and transfer of anion (micellar extraction) to the organic phase, thereby providing a higher rate of reactive intermediate generation; e.g. trichloromethyl anion generation.

In the present reactions, the aqueous inorganic salt reservoir contains the $OH^-$ nucleophile supplied by an alkali or alkaline earth metal hydroxide and it is this nucleophile which must be contacted with the organic phase substrate for the essential generation of carbene or naked, trihalomethyl anion, which in turn reacts, by 1,2- or 1,4- addition, or $S_n2$ displacement mechanisms, with the normally liquid, olefinically unsaturated coreactant dissolved in the organic substrate employed as the organic phase.

The cyclopropanation catalysis of the present process is illustrated by the following equations wherein sodium hydroxide is selected as the water soluble inorganic salt; chloroform is selected as the organic substrate, ethylene is the organic coreactant and a quarternary chloride ($Q^+Cl^-$) represents the quarternized catalyst.

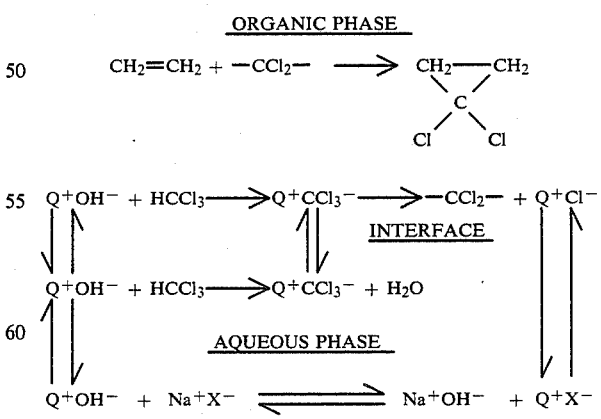

When the unsaturated organic coreactant contains a carbonyl group, eg. methyl acrylate, the reaction in the organic phase proceeds mainly by the following 1,4 Michael addition

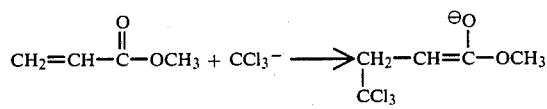

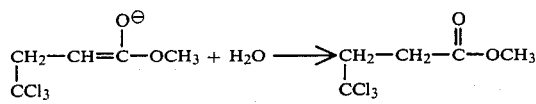

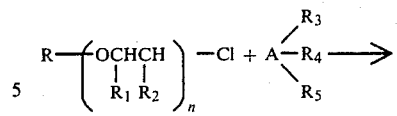

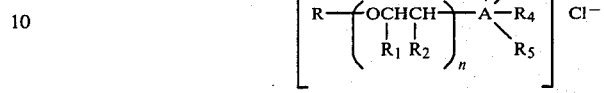

As shown in the above mechanistic representation the initial anion exchange takes place in the aqueous phase, preferentially at the interface, to provide a soluble quaternized hydroxy nucleophile which partitions into both organic and aqueous phases through the surfactant modified interface. The quaternary hydroxide nucleophile activated by solubilization in the organic phase deprotonates the solvent and exchanges anions with the organic substrate at the interface by acid/base deprotonation, to form the trihalomethyl anion which in turn dissociates to produce the corresponding dihalocarbene radical or reacts by addition to the olefinic carbonyl compound followed by protonation. The original hydrophilic quaternary halide is reformed as a by-product and enters the aqueous phase for further anion exchange. In the reaction with a hydrocarbon olefin, the dihalocarbene reacts with the olefin coreactant in the organic phase to provide the desired cyclopropanation product of the process. The above equations are intended only to illustrate a mechanism for the rate enhanced phase transfer reactions of th is invention and are not to be construed as limiting the scope of this invention which is broadly applicable to all rate limited liquid/liquid phase transfer of reaction intermediates.

According to this invention the aqueous phase comprises an inorganic salt capable of generating a hydroxy anion. Although sodium and potassium hydroxides are most preferred, it is to be understood that other inorganic hydroxides, such as any alkali metal or alkaline earth metal hydroxide, can also be used. The inorganic salt is generally maintained in the aqueous phase at a concentration of between about 5% and about 60%, preferably between about 25% and about 50%, and the volume ratio of aqueous phase to organic phase is broadly between about 1:1 and about 1:3, more desirably between about 1:2 and about 1:3.

The preferred quaternary ammonium catalysts of the present invention are those in which R is alkyl containing from 8 to 18 carbon atoms or an alkyl substituted phenyl radical wherein said alkyl substituent contains from 4 to 10 carbon atoms and may occupy 1 or 2 positions on the phenyl ring; A is a nitrogen atom; halo$^-$ is a chloride anion and $R_3$, $R_4$ and $R_5$ are independently alkyl of 1 or 2 carbon atoms or phenyl or one of $R_3$, $R_4$ and $R_5$ is hydrogen and/or $\beta$-sulfoethyl sodium salt. The quaternary salt catalysts are easily and conventionally prepared by reacting the corresponding polyoxyalkylene monochloride with the corresponding primary, secondary or tertiary amine or phosphine for a period of 6 to 20 hours at a temperature of between about 100° C. and about 160° C. under a pressure of from about 14 to about 60 psig. The reaction proceeds by $S_n 2$ displacement as illustrated by the equation:

wherein Br$^-$ can be substituted for Cl$^-$ in an identical reaction. The reaction may be carried out in aqueous solution wherein the amine or phosphine is present in a concentration of between about 10 to about 35% in an inert solvent such as water, isopropanol, or other inert solvent. A more detailed discussion for the preparation of the present quarternized catalyst compounds is found in copending patent application Ser. No. 096,991, filed Nov. 23, 1979 on Quarternary Drivatives of Polyoxy Alkylenes and also in U.S. Pat. No. 2,745,877; U.S. Pat. No. 3,404,183 and The Journal of the American Chemical Society, Volume 93, page 195, 1971.

The concentration of the quarternary catalysts in the initial aqueous phase is maintained between the critical micell concentration and 1%, preferably between about 0.1 and about 0.5%; as is consistent with a mole ratio of from about 0.0001:1 to about 0.01:1, preferably from about 0.0003:1 to about 0.0015:1, of quarternized catalyst with respect to organic substrate in the system.

Organic substrates which are suitably employed in the present phase transfer reactions are the iodides, chlorides or bromides of methane and mixed halogenated methanes, preferably a normally liquid halogenated methane, which are capable of generating a carbene intermediate. Specific examples of such substrates include chloroform, bromoform, iodoform, dichloromethane, and combinations of these. The substrate is present as a carrier for the olefinically unsaturated reactant in the organic phase and is present in a mole ratio of between about 5:1 and 20:1, preferably 10:1 and 15:1, with respect to said olefinically unsaturated coreactant.

The olefinically unsaturated coreactant of the present process includes any of the electron rich substances containing olefinic unsaturation either, as an aliphatic or cycloaliphatic olefin or as an olefinic group, or as a side chain. Specific examples of such olefinic substances include styrene, cyclohexene, phenylpropene, indene, thiophene, methyl acrylate, methyl methacrylate, 1-octene, 1-hexene, 1,4-dichlorobutene-2, isobutene-2, conjugated dienes such as 1,3-butadiene, 2,4,6-cyclooctatriene, cyclopentadiene, vinylbenzenes, and any of those olefins designated on pages 23 through 42 of PHASE TRANSFER CATALYSIS IN ORGANIC SYNTHESIS, Volume 4 by W. P. Weber and G. W. Gokel, Springer-Verlag., 1977 and in the addition reactions and substitution reactions illustrated therein on pages 49 through 56. The present phase transfer reactions also include deuterium phase reactions discussed in Phase Transfer Catalysis by C. M. Starks and C. Liotta, Academic Press, 1978, pages 341–343.

The reactions of the present invention are carried out under relatively mild conditions including a temperature of between about 20° and about 100° C. preferably between about 25° and about 75° C.; under a pressure of about 14 psig. to about 50 psig.; more desirably, from about 14 psig. to about 25 psig. for a period of from about 0.5 to about 12 hours, more often between about 1 and about 6 hours.

Having thus broadly described the aspects of the present invention, reference is now had to the following examples which illustrate preferred embodiments but which are not to be construed as limiting to the scope of the invention as more broadly defined in the foregoing description and in the appended claims.

PREPARATION OF QUATERNIZED CATALYST

EXAMPLE 1

Preparation of
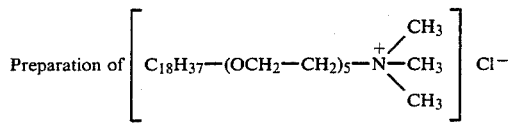

To a 3 liter round bottom flask, equipped with mechanical stirrer, thermometer, dropping funnel and condenser attached to a caustic soda scrubber, was charged 1967 gms. (4.0 moles) of 1-octadecanol ethoxylated to hydrophilic/lipophilic balance (HLB) of about 9.7. To this, 525 gms. of $SOCl_2$ (4.4 moles) was added at a rate sufficient to maintain the reaction temperature between 40-55° C. When all the $SOCl_2$ had been charged, the reaction mixture was heated to 110°-115° C. with a nitrogen purge and held at this temperature for ½ hour. Examination of the IR spectra indicated the absence of any unreacted nonionic compound. The chlorosulfite was then decomposed by purging with air at 90°-105° C. for a period of 3-4 hours at which point the inorganic chloride concentration was reduced to 0.5%. The product had a golden yellow color (VCS8) and analyzed for 6.9% organic chloride (7.0% theory, M. Wt.=509) and 0.2% inorganic chloride. The intermediate product yield was 1,995 gms. or 98% of $C_{18}H_{37}(OCH_2CH_2)_5Cl$.

A clean and dry 1 gal. autoclave was charged with 254 gms. (0.50 mole) of the above product, 200 gms. of isopropyl alcohol, 8.0 gms. (0.10 mole) of 50% caustic soda and 145 gms. (0.60 mole) of 25% trimethylamine. The reaction mixture was heated to 110-115° C. with agitation for 10 hrs., after which the sample was cooled to 50-60° C. and 600 gms. (99%) of quaternized product recovered. The conversion to quaternary was 90% and a yield of 94% (by chloride) had been obtained.

EXAMPLE 2

Preparation of
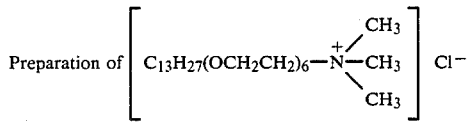

To a 1 liter round bottom flask equipped with mechanical stirrer, thermometer, dropping funnel and condenser attached to a caustic soda scrubber was charged 325 gms. (0.70 mole) of $C_{13}H_{27}(OCH_2CH_2)_6OH$, M. Wt. 464, (Emulphogene BC-610) and 104 gms. (0.87 mole) of $SOCL_2$ at 25° C. An exotherm occured and the addition was continued at 45°-55° C. with occasional cooling. When the addition of $SOCl_2$ was completed the mixture was further heated to 115°-120° C. for 30 minutes after which IR spectra showed no OH band at 3500 $cm^{-1}$. Heating was continued at 100-105° C. with air purging for 3 hrs. and the mixture was tested for completion of the reaction (0.02% $Cl^-$ by Volhard).

The product had a color of VCS=11-12 and analyzed for 7.4% organic chlorine (7.4% theory, M. Wt. —482.5) and contained less than 0.1% inorganic chloride. The product yield was 330 gms. or 97.5% of $C_{13}H_{27}(OCH_2CH_2)_6Cl$.

A clean 1 gal. autoclave was charged with 600 gms. the chloride product (1.24 moles) and 500 gms. of 25% aqueous trimethylamine (2.11 moles). The reaction mixture was heated to 110°-115° C. (45-50 psig) for 10 hrs., the reaction mixture cooled to 40° C. and evaluated for inorganic chloride (4.0%=100% conversion). A portion of the product (480 gms.) was diluted with 400 gms. water and heated to 70°-75° C. with air purging for 1 hr. to remove the excess trimethylamine (TMA) and the resulting product analyzed as follows: 28.7% quaternary (by $HClO_4$ method), 30.7% quaternary (by reverse Methylene Blue titration) based on M. Wt.=541.5; 1.64% nonionic; 0.3% TMA; 0.1% TMA.HCL; and 66.6% $H_2O$.

EXAMPLE 3

Preparation of
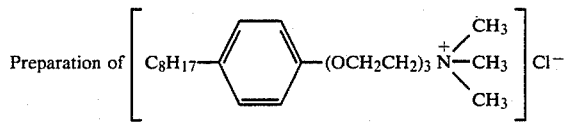

A clean 1 gal. autoclave was charged with 338 gms. (0.95 mole) of

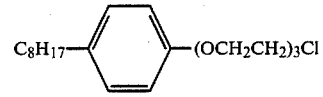

(Igepal CA-420 chloride) and 500 gms. of 25% aqueous trimethylamine (2.11 mole). The reaction mixture was heated to 110°-115° C. (45-50 psig) for 10 hrs., cooled to 40° C. and analyzed for inorganic chloride (3.8%=95% conversion). Excess trimethylamine was removed by purging air through the sample at 65°-70° C. for 1 hr. after transfer to 1 liter round bottom flask equipped with condenser thermometer and mechanical stirrer. The product analyzed as follows: 47.4% quaternary (by $HClO_4$ method), 49.24% (by reverse Methylene Blue titration) based on M. Wt.=415.5; 8.1% nonionic 0.56% TMA; 0.65% TMA.HCl; and 42.3% water. The product yield was 722 gms. or 93%.

EXAMPLE 4

Preparation of
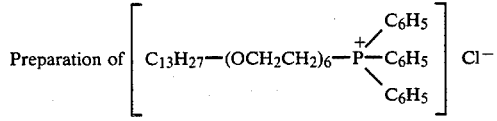

A 1 gal. autoclave was charged with 241 g. (0.5 mole) of $C_{13}H_{27}(OCH_2CH_2)_6Cl$ and 144 g. (0.55 mole) of triphenyl phosphine in 350 g. of tetrahydrofuran. The reaction mixture was agitated and heated to 110°-120° C. for 15 hours, then cooled to 35° C. and the resulting viscous liquid removed. The tetrahydrofuran was stripped on a rotary evaporator leaving 388 g. of product which solidified on standing. This material analyzed as follows: 97.2% phosphonium salt, 1.2% nonionic.

EXAMPLE 5

Preparation of 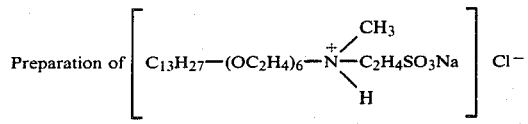

Into a 1 gal. autoclave was charged 242 g. (0.5 mole) of C$_{13}$H$_{27}$(OCH$_2$CH$_2$)$_6$Cl and 360 g. (0.55 mole) of N-methyl taurine in the form of a 24.6% active aqueous solution. The reaction mixture was agitated and heated to 140°–150° C. for 8 hours, then cooled to 50° C. and discharged as a viscous paste. The product analyzed as follows: 56.4% quaternary (by HClO$_4$ method), 45.6% quaternary (by reverse methylene Blue titration) based on a molecular weight of 644; 2.7% nonionic; 6.3% N-methyl taurine.HCl and 45.2% water. The conversion to quaternary was 86% with 99% conversion of chlorine capped nonionic (based on Cl$^-$).

EXAMPLE 6

Preparation of

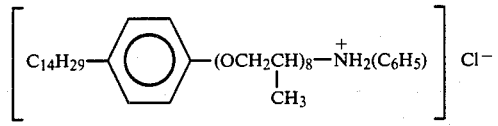

Into a 1 gal. autoclave was charged 0.5 mole (387 gms) of

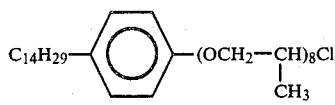

and 0.55 mole of 25% isopropyl alcohol solution of aniline. The autoclave is sealed and heated to about 115°–120° C. for 16 hours and allowed to cool to room temperature. The reaction mixture is withdrawn from the autoclave and solvent removed by evaporation. The substitution product

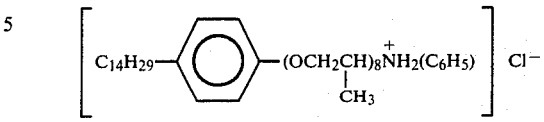

is recovered in high yield.

EXAMPLE 7

The activity of the following catalysts was determined by the exotherm developed in a reaction system comprising a 50% aqueous solution of sodium hydroxide as the aqueous phase and an equal volume of an organic mixture comprising chloroform and styrene in a mole ratio of 13:1. The mole ratio of styrene to 50% NaOH was maintained at 1:5. Each experiment was carried out in a 1 liter glass beaker in a constant temperature bath (26° C.) equipped with a thermometer to measure temperature changes, i.e. exotherm changes, which indicate an anion exchange between the catalytic halide and the NaOH.

The quaternized catalyst(0.5% of the NaOH solution), was added to the aqueous phase at a temperature of 26° C. and stirred briefly. The temperature in the aqueous phase was observed after 15 minutes, and the following results were reported. The catalysts indicated in the following Table A were compared with a representative phase transfer catalyst, Aliquat 336 supplied by General Mills.

TABLE A

| Catalyst | Exotherm | Organic Soluble Catalytic Product |
|---|---|---|
| C$_8$H$_{17}$—⌬—(OC$_2$H$_4$)$_3$—$\overset{+}{\text{N}}$(CH$_3$)$_3$Cl$^-$ | 12–15° | C$_8$H$_{17}$—⌬—(OC$_2$H$_4$)$_3$—$\overset{+}{\text{N}}$(CH$_3$)$_3$OH$^-$ |
| C$_{13}$H$_{27}$—(OC$_2$H$_4$)$_6$—$\overset{+}{\text{N}}$(CH$_3$)$_3$Cl$^-$ | 12–15° | C$_{13}$H$_{27}$—(OC$_2$H$_4$)$_6$—$\overset{+}{\text{N}}$(CH$_3$)$_3$OH$^-$ |
| C$_{13}$H$_{27}$—(OC$_2$H$_4$)$_6$—$\overset{+}{\text{N}}$(CH$_3$)(H) C$_2$H$_4$SO$_3$Na · Cl$^-$ | 12–15° | C$_{13}$H$_{27}$—(OC$_2$H$_4$)$_6$—$\overset{+}{\text{N}}$(CH$_3$)(H) C$_2$H$_4$SO$_3$Na · OH$^-$ |
| C$_{18}$H$_{37}$—(OC$_2$H$_4$)$_5$—$\overset{+}{\text{N}}$(CH$_3$)$_3$Cl$^-$ | 15–20° | C$_{18}$H$_{37}$—(OC$_2$H$_4$)$_5$—$\overset{+}{\text{N}}$(CH$_3$)$_3$OH$^-$ |
| (C$_8$H$_{17}$)$_3$—$\overset{+}{\text{N}}$(CH$_3$)Cl$^-$* | 2–3° | (C$_8$H$_{17}$)$_3$—$\overset{+}{\text{N}}$(CH$_3$)OH$^-$ |

*(Aliquat 336)

The significantly lower exotherm produced by Aliquat 336 is partially due to a lower chemical potential for anion exchange. The interfacial tension in a 1:1 volume ratio of 50% caustic to chloroform is 30.6 dynes/cm at 25° C.; whereas in the presence of 0.1%

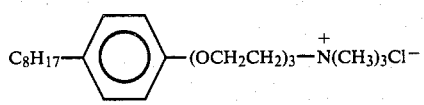

the interfacial tension is 1.4×10$^{-2}$ dynes/cm, as measured by a spinning-drop interfacial tensiometer. This enhancement of anion exchange and phase transport is reflected in the comparative experiments in Example 8.

EXAMPLE 8

A comparative experiment was run using 0.1 mole % of Aliquat 336 and 0.1 mole %

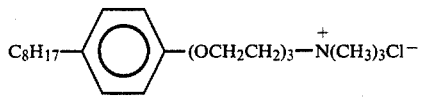

as the catalyst, based on the weight of chloroform which was used as the trapping agent for dichlorocarbene. The ratio of 50% caustic to chloroform was 1:3 and the chloroform layer contained 10 mmoles of styrene for each experiment. A 250 ml. round bottom flask was charged with 150 g. of $CHCl_3$ and 1 g. (10 mmoles) of styrene. The specified catalyst (0.1 mole % based on the $CHCl_3$ charge) was predissolved in 50 g. of 50% NaOH and transferred to a dropping funnel. The catalyst solution was quickly added to each of the styrene/$CHCl_3$ mixtures under equivalent agitation and an aliquot was taken at various intervals to determine the relative conversion of styrene to the cyclopropane adduct.

The emulsion obtained was broken by chilling the reaction flask in a dry ice trap. The aliquot was removed from the chloroform layer which was then frozen prior to chromographic analysis.

The sample was analyzed for styrene and cyclopropane adduct by chromatography in a 5 foot, 20% SE-30 column coated on Chromosorb WAW/DMCS with a temperature programming of 110°-175° C. at 6° C. per minute. Detection was by thermal conductivity with relative response correction applied. The mole ratios of cyclopropane to styrene at various intervals are reported in Table B.

TABLE B

Catalysis in Cyclopropanation of Styrene

| Reaction Time (hrs.) | Ratio of Product/Styrene $[C_8H_{17}(C_6H_4)-(OC_2H_4)_3-\overset{+}{N}(CH_3)_3]Cl^-$ | Aliquat 336 |
|---|---|---|
| 0.75* | 0.46:1 | 0.006:1 |
| 1.25 | 1.99:1 | 0.106:1 |
| 1.75 | 4.13:1 | 0.18:1 |
| 2.25 | 6.25:1 | 0.23:1 |
| 2.75 | 13.9:1 | 0.32:1 |
| 3.25 | 32.3:1 | 0.37:1 |
| 4.0 | 99:1 | 0.64:1 |
| 5.0 | 99:1 | 1.00:1 |
| 6.0 | 99:1 | 1.56:1 |
| 7.0 | 99:1 | 2.17:1 |

*After 0.75 hrs. both samples were heated to ~40° C. for the duration. From the above results, it is shown that the relative reactivity of the present quaternary vs. Aliquat 336 is 5.6:1.

EXAMPLE 9

The following experiments illustrate the effect of quaternary catalyst structure on the reaction rate.

The experiment of Example 8 was repeated with the same catalyst concentration at a starting temperature of 40° C. The reaction mixture exothermed to 58° C. and samples were withdrawn at 1.25 hours. The molar ratio of cyclopropanated styrene product to styrene is tabulated for different structural species in Table C.

TABLE C

Phase Transfer Catalyst Structure-Activity Relationship

| | Time | Cyclopropane/ Styrene |
|---|---|---|
| $(C_8H_{17})_3\overset{+}{N}(CH_3)_3Cl^-$ | 1.25 hrs. | 18/1 |
| $C_8H_{17}(C_6H_4)-(OC_2H_4)_3\overset{+}{N}(CH_3)_3Cl^-$ | 1.25 hrs. | 70/1 |
| $C_8H_{17}(C_6H_4)-(OCHCH_2)_4\overset{+}{N}(CH_3)_3Cl^-$<br>$\quad\quad\quad\quad\quad\quad\quad\quad\quad |$<br>$\quad\quad\quad\quad\quad\quad\quad\quad\quad CH_3$ | 1.25 hrs. | 85/1 |
| $C_{18}H_{37}(OC_2H_4)_5\overset{+}{N}(CH_3)_3Cl^-$ | 1.25 hrs. | 279/1 |

From the above data, the following relative reactivities of the various quaternized catalysts were found to be

| | Rel. Activity |
|---|---|
| Aliquat 336 $(C_8H_{17})_3\overset{+}{N}(CH_3)_3Cl^-$ | 1.00 |
| Quaternary of Example 7<br>$C_8H_{17}(C_6H_4)-(OC_2H_4)_3\overset{+}{N}(CH_3)_3Cl^-$ | 3.83 |
| Quaternary using Propylene oxide<br>$C_8H_{17}(C_6H_4)-(OCHCH_2)_4\overset{+}{N}(CH_3)_3Cl^-$<br>$\quad\quad\quad\quad\quad\quad\quad\quad |$<br>$\quad\quad\quad\quad\quad\quad\quad CH_3$ | 4.67 |
| Quaternary of Example 8<br>$C_{18}H_{37}(OC_2H_4)_5\overset{+}{N}(CH_3)_3Cl^-$ | 15.2 |

It is to be understood that, in the above Examples 8 and 9, any of the other quaternized catalysts of this invention can be substituted to provide similar benefits. For example, the catalyst of Example 4 is substituted in Example 8 with substantially the same improvement in conversion to product is obtained. Substitution of bromide for chloride in the quaternary catalysts of this invention did not substantially alter the catalytic activity.

What is claimed is:

1. In a liquid/liquid phase reaction process involving an organic phase and an aqueous phase, insoluble in said organic phase, said aqueous phase containing an aqueous solution of an inorganic salt having an OH⁻ anion the improvement which comprises contacting said inorganic salt with an effective OH⁻ anion exchanging amount of a quaternized phase transfer catalyst having the formula

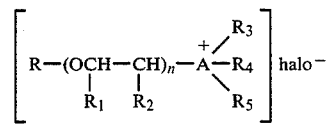

wherein
R is alkyl having 8 to 30 carbon atoms, blends thereof or alkyl-substituted phenyl of 10 to 24 carbon atoms;

n has a value of from 2 to 14 and includes mixtures within said range;

$R_1$ and $R_2$ are hydrogen atoms or one of $R_1$ and $R_2$ is methyl;

$R_3$, $R_4$ and $R_5$ are independently hydrogen, alkyl radical of 1 to 6 carbon atoms or phenyl or one of $R_3$, $R_4$ and $R_5$ is β-ethyl-alkali metal sulfonate;

A is a phosphorous or a nitrogen atom; and halo is a chlorine or bromine ion.

2. The process of claim 1 wherein said quaternized catalyst has the formula:

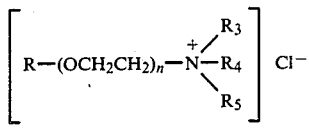

wherein R is alkyl of 10 to 18 carbon atoms or

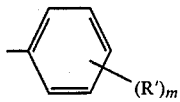

where R' is alkyl of 4 to 10 carbon atoms and m has a value of 1 to 2; $R_3$, $R_4$ and $R_5$ are independently hydrogen, alkyl of 1 or 2 carbon atoms and n has a value of 2 to 14 and includes mixtures thereof.

3. The process of claim 2 wherein said quaternized catalyst has the formula:

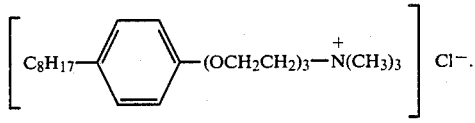

4. The process of claim 2 wherein said quaternized catalyst has the formula:

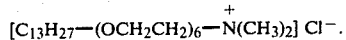

5. The process of claim 2 wherein said quaternized catalyst has the formula:

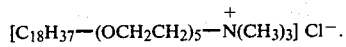

6. The process of claim 2 wherein said quaternized catalyst has the formula:

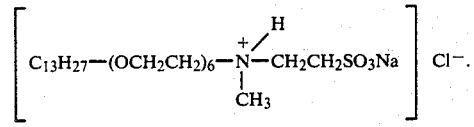

7. The process of claim 2 wherein said inorganic salt is an alkali metal hydroxide.

8. The process of claim 7 wherein said inorganic salt is sodium hydroxide.

9. The process of claim 1 wherein an aqueous solution of between about 5% and about 60% of an inorganic hydroxy anion generating salt forms an aqueous phase and between about 1% and about 10% of an olefinically unsaturated compound dissolved in a haloalkane capable of generating a carbene radical forms said organic phase, and wherein contact between the hydroxy anion of said salt and the haloalkane of said organic phase is effected by said addition of said quaternized phase transfer catalyst to said aqueous phase.

10. The process of claim 9 wherein the olefinically unsaturated compound is styrene and the haloalkane is chloroform.

11. The process of claim 9 wherein the mole ratio of said haloalkane to said olefinically unsaturated compound is between about 5:1 and about 20:1 and the quaternized catalyst is added to the aqueous phase in a mole ratio of from about 0.0001:1 and about 0.01:1 with respect to said haloalkane.

* * * * *